United States Patent [19]
Iglesias et al.

[11] Patent Number: 5,716,335
[45] Date of Patent: Feb. 10, 1998

[54] ANKLE BRACE WITH ADJUSTABLE HEEL STRAP

[75] Inventors: Joseph M. Iglesias, Agoura, Calif.; Tracy E. Grim, Broken Arrow, Okla.; William K. Arnold, Longmeadow, Mass.; Eric E. Johnson, Thousand Oaks, Calif.

[73] Assignee: Royce Medical Company, Camarillo, Calif.

[21] Appl. No.: 521,091

[22] Filed: Aug. 29, 1995

Related U.S. Application Data

[63] Continuation-in-part of Ser. No. 99,237, Jul. 29, 1993, Pat. No. 5,445,602.

[51] Int. Cl.$^6$ ..................................................... A61F 5/00
[52] U.S. Cl. ..................................... 602/27; 602/16
[58] Field of Search .................... 602/5, 16, 27–29; 128/882, 892

[56] References Cited

U.S. PATENT DOCUMENTS

| | | | |
|---|---|---|---|
| 1,418,283 | 6/1922 | Cameron | 602/16 |
| 3,834,377 | 9/1974 | Lebold . | |
| 4,821,743 | 4/1989 | Wetz | 602/27 X |
| 4,834,078 | 5/1989 | Biedermann . | |
| 4,964,402 | 10/1990 | Grim et al. | 602/27 X |
| 4,977,891 | 12/1990 | Grim | 602/27 |
| 5,014,691 | 5/1991 | Cueman et al. . | |
| 5,031,607 | 7/1991 | Petus | 602/27 |
| 5,044,360 | 9/1991 | Janke . | |
| 5,069,202 | 12/1991 | Prock | 602/27 |
| 5,088,480 | 2/1992 | Wang . | |
| 5,094,232 | 3/1992 | Harris et al. . | |
| 5,209,722 | 5/1993 | Miklaus et al. . | |
| 5,226,875 | 7/1993 | Johnson | 602/27 |
| 5,242,378 | 9/1993 | Baker | 602/27 X |
| 5,242,379 | 9/1993 | Harris et al. . | |
| 5,366,439 | 11/1994 | Petus | 602/27 |
| 5,445,603 | 8/1995 | Wilkerson | 602/27 |
| 5,472,411 | 12/1995 | Montag et al. . | |
| 5,527,269 | 6/1996 | Reithofer | 602/27 |

*Primary Examiner*—Linda C. Dvorak
*Attorney, Agent, or Firm*—Oppenheimer Poms Smith

[57] ABSTRACT

An improved ankle brace may have two relatively rigid side supports, the outer edge portion of the lower area of the side supports, adjacent to the ankle being covered with a flexible or resilient material. The flexible resilient material may be permanently secured to the side supports by bonding, mechanical interlocking, or by any other suitable arrangements. Additional resilient flexible material may be placed on the interior surface of the side supports to improve the fit and comfort of the brace around the user's lower leg. The rigid side supports may be of an open type with the resilient flexible material extending across the side supports and beyond the edges thereof. The lower area of the side supports may include a pivoting mechanism to adjustably receive heel straps. Each of the side supports may include a structural frame that surrounds but does not cover the ankle or malleolus.

26 Claims, 8 Drawing Sheets

ANKLE BRACE WITH ADJUSTABLE HEEL STRAP

CROSS-REFERENCE TO RELATED APPLICATIONS

This application is a continuation-in-part of application Ser. No. 08/099,237, filed Jul. 29, 1993, now U.S. Pat. No. 5,445,602, issued Aug. 29, 1995.

FIELD OF THE INVENTION

The present invention relates to an improved orthopaedic device, and specifically to an ankle brace for stabilizing an ankle before or after injury. In particular, the ankle brace of the present invention stabilizes the ankle against inversion and eversion and anterior subluxation while allowing normal dorsiflexion and plantarflexion movement. Further, the invention includes a heel strap adjustably attachable to the braces for providing appropriate fit for heels of various widths.

BACKGROUND OF THE INVENTION

After injury to an ankle, such as a fracture or severe ankle sprain, it is often necessary to completely immobilize the injured ankle through the use of a molded plaster or resin cast. Once the injury has been stabilized, however, recovery may be accelerated by removing the molded plaster or resin cast and replacing it with a removable ankle brace so that the ankle can be exercised while healing.

Even if the injury is not severe enough to warrant complete immobilization of the ankle, it is still sometimes necessary to use a functional wailing brace to stabilize the ankle against inversion (the foot rolling inward), eversion (the foot rolling outward) and/or subluxation (partial dislocation) while still allowing the normal dorsiflexion and plantarflexion movement of the ankle.

A variety of ankle braces, walking casts and other orthopaedic ankle apparatuses have previously been proposed. For instance, in my prior U.S. Pat. No. 4,977,891, granted Dec. 18, 1990, and entitled "Variable Support Ankle Brace," an ankle brace comprising two relatively rigid side supports with inflatable bladders attached to them is described. Other ankle braces including air inflatable bladders are shown in Glenn W. Johnson, Jr.'s U.S. Pat. Nos. 4,280,489 and 4,628,945. These prior art devices proposed by Johnson are intended to be worn within a separate shoe and are also inflatable.

Thermal treatment has been made available with the use of orthopaedic gel pads which tend to mold themselves to fit the area they are applied to, providing a level of comfort and padding as well as providing thermal treatment of the affected area. One such pad is shown in my U.S. Pat. No. 5,027,801.

Prior art walking braces have employed rigid support shells which may engage and irritate, pinch and damage the skin within the shoe. For instance, the rigid ankle brace shown by the U.S. Pat. No. 4,834,078 is made of "high-performance composite material." A principal object of the present invention is to effectively avoid this problem with a flexible heel strap which is adjustably attachable to the braces.

SUMMARY OF THE INVENTION

In accordance with one broad aspect of this invention, the outer edge portions of at least the lower area of the side supports, adjacent to the ankle, are formed of a flexible material.

In accordance with another broad aspect of this invention, each entire side support is bonded to or integrally associated with flexible material, slightly larger in size but similar in shape to the side support. Both of these side support designs improve the fit and the comfort of the brace around the user's lower leg.

In accordance with yet another broad aspect of this invention, a more flexible material is formed around a more rigid material. In an alterative implementation, the more flexible material is formed with protrusions/tab and/or receptacles for protrusions/tabs formed in the more rigid material. This allows the more flexible material and more rigid material to be mated and interlocked to one another.

In accordance with another broad aspect of this invention, the more rigid material is hollowed out in certain areas to form a frame. The frame is covered with the more flexible material and the resultant structure is employed as an ankle brace.

Accordingly, it is a primary object of the present invention to prevent undesired inversion, eversion and anterior subluxation while allowing plantarflexion and dorsiflexion of the ankle, without irritating or pinching the skin.

Another object of this invention is to provide a more comfortable ankle brace which will firmly support an injured lower leg. As discussed above, this may be achieved by a combination of more and less flexible materials, using rigid or semi-rigid structural frame supporting the flexible resilient material. In addition, this may be achieved by designing the rigid structural frame such that hollowed out portions of the frame correspond to the ankle or malleolus area. Such design of the structure frame will allow the protruding ankle to be covered only by the flexible material while the surrounding frame provides the necessary support and control, thus increasing the comfort and effectiveness of the brace.

Yet another goal of this invention is to accommodate various sizes and widths of feet by providing a flexible heel strap, the effective length of which can be adjusted. Further, the flexible heel strap may be pivotally attached to the bottom of the side support, thus permitting front-to-rear mobility of the ankle, while still limiting lateral movement. The pivot structure is preferably in the form of a rotatable pivot disc, to which the strap may be adjustably secured.

The foregoing and other features and advantages of the present invention as well as a more complete understanding thereof will be made apparent from a consideration of the following detailed description in connection with the accompanying drawings.

DETAILED DESCRIPTION OF THE PREFERRED EMBODIMENTS

Initially, it is noted that the drawings in the present case relate to two inventions, with the present invention being described in detail in connection with FIGS. 7 and 9–18. FIGS. 1–8 are included for convenience as disclosing a complete ankle support assembly as shown in FIG. 7. The embodiments of FIGS. 9–18, illustrating the principles of this invention, may be used as side supports 18, 20 in the configuration of FIG. 7.

Figure 1:
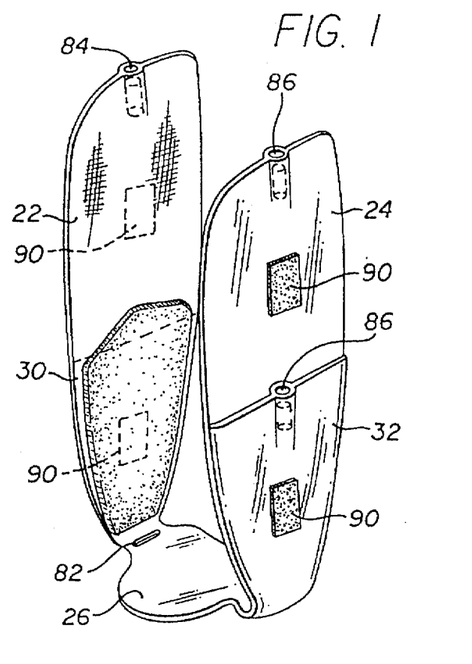
FIG. 1 is a diagrammatic, perspective view of a bladder and pump arrangement for an ankle brace.
Figure 2:
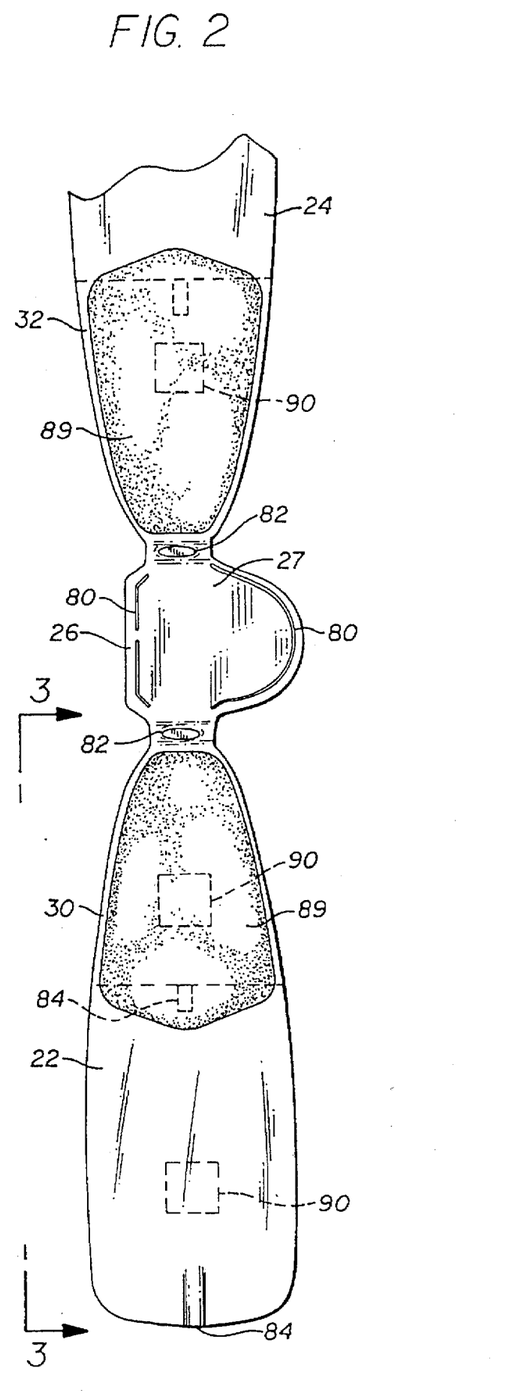
FIG. 2 is a partial unfolded top plan view of the inside surface of the bladder and pump arrangement of FIG. 1.
Figure 6:
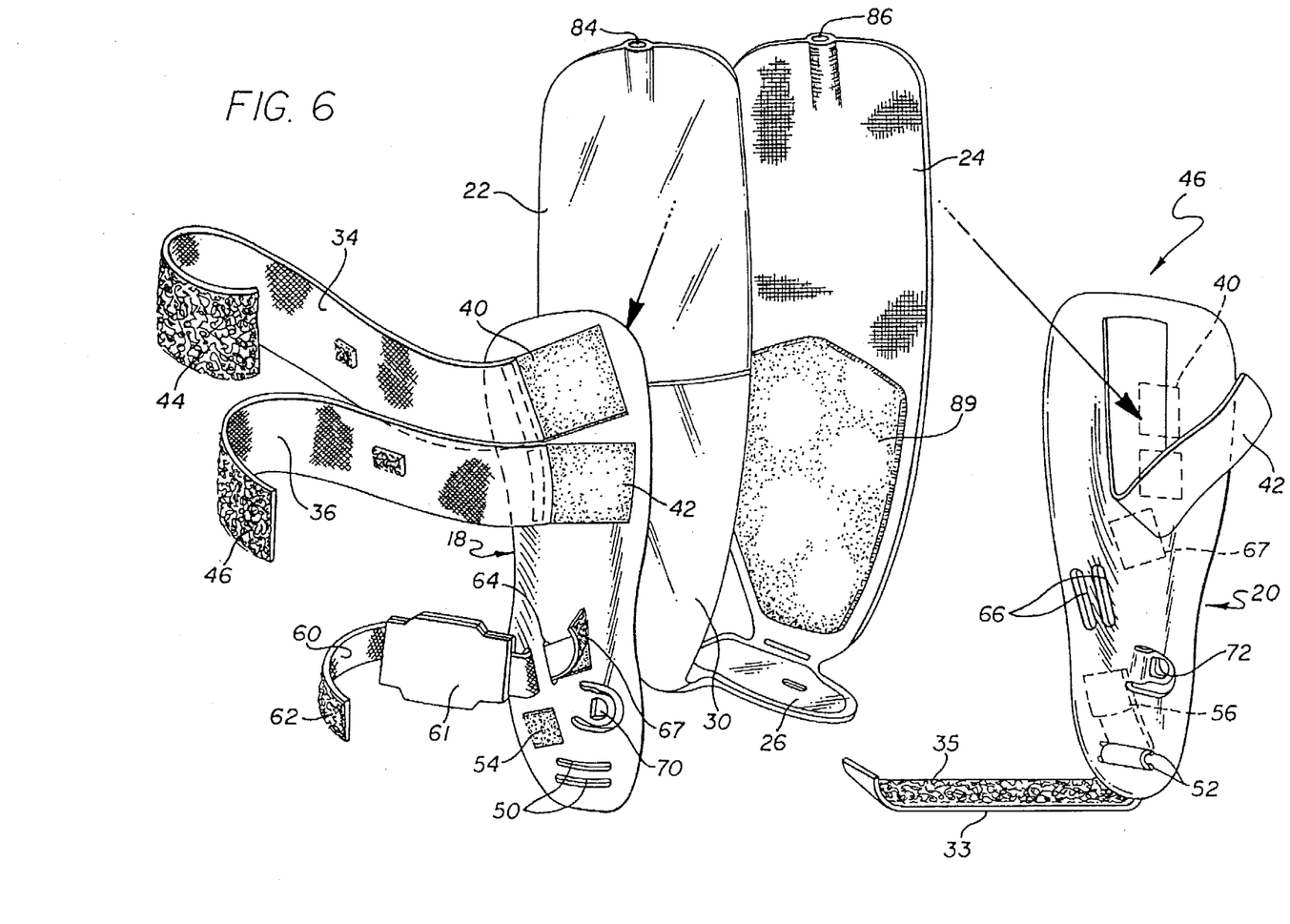
FIG. 6 is an exploded perspective view of an embodiment of an improved ankle brace.
Figure 7:
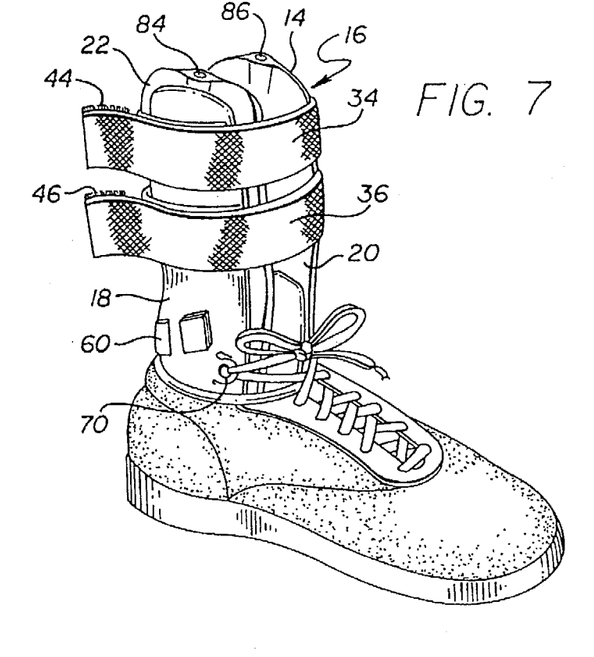
FIG. 7 is a perspective view of an embodiment of the ankle brace of the present invention fitted and properly secured in association with a shoe including laces.
Figure 8:
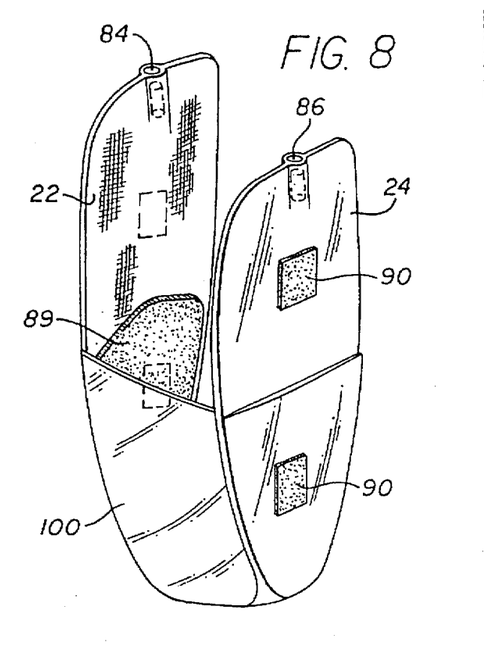
FIG. 8 is diagrammatic, perspective view of another embodiment of a bladder and pump arrangement.

With reference to FIGS. 6 and 7, an improved ankle brace 16 includes a pair of side support members 18 and 20 preferably made of vacuum molded plastic, for example, nylon or rigid polypropylene, having sufficient thickness and other properties so that they are relatively stiff or rigid; and they are shaped so as to fit about the lower leg and ankle and are approximately eight to ten inches long. Also included are two main inflatable bladders 22 and 24 and a pump 26 which are interconnected and formed with one welding process. The inflatable bladders 22 and 24 can be attached to the side supports 18 and 20 using a Velcro-type fabric, double sided adhesive or any other suitable means. Additional inflatable bladders 30 and 32 as shown in FIGS. 1 and 2, placed distally upon the main inflatable bladders 22 and 24.

Interconnecting the two side support members 18 and 20 is a bottom strap 33. The bottom strap may include a surface 35 of Velcro material and with the bottom strap being adjustable through the use of double openings 50 and 52 located near the bottom end of the side supports 18 and 20. The ends of the bottom strap 33 may be fixed in position with the use of additional Velcro material 54 and 56 located on the outside of the side support members 18 and 20. Specifically, the adjustment is accomplished by positioning the ends of the strap 33 to extend from the outside of each support member 18 and 20 through opening 50 or 52 and then through the other one of the openings 50 or 52 and then attached by the Velcro material 54. Thus, the proper distance may be easily adjusted between the side support members 18 and 20 at the lower most portion.

The side supports 18 and 20 may be securely attached around the lower leg and ankle just below the calf area using two strap members 34 and 36. These strap members 34 and 36 also include Velcro portions 40 and 42 on their outer surfaces, and with Velcro material 44 and 46 at the end portions of the straps 34 and 36. The Velcro 40 and 42 is attached to the side support 18 or 20. As shown in FIG. 7, these straps 34 and 36 may be tightly drawn around the lower leg using the Velcro material so that the ankle brace securely and firmly supports the ankle.

The ankle brace includes, in addition to the strap arrangement set forth above, a counter strap 60 which is similar in construction to the bottom strap 33. Specifically, the counter strap 60 may include a cushioning pad 61 and an inner surface covered with Velcro material 62 and with the strap 60 passing through double openings 64 in the side support 18 and double openings 66 in the other side support 20. An additional piece of Velcro material 67 is attached to side support member 18 and another piece of Velcro material 67 is attached to side support 20. By having this arrangement the counter strap 60 may be adjusted in a similar manner to the bottom strap 33 to prevent the back portion of the side support means 18 and 20 from twisting or flexing outward at the lower end of the ankle brace 16 to compress the distal ⅓ to ½ of the brace.

The ankle brace may incorporate a lace fastening means similar to that set forth in detail in Grim, U.S. Pat. No. 4,844,094 to insure that the side supports 18 and 20 do not twist or flex outward and to more properly stabilize and compress the ankle against inversion, eversion and anterior subluxation. It is preferred, as shown in FIG. 7, that the lace fastening arrangement in the present invention comprises a hole or slot 70 and 72 integrally molded at the bottom end of each side support member 18 and 20. It is to be appreciated, however, that other attachment means such as those set forth in the U.S. Pat. No. 4,844,094 may be used.

FIGS. 1 and 2 illustrate an inflatable bladder and pump arrangement. The foot pump 26 is comprised of an open cell foam and or a flexible hollow or curved resilient material (for example, rubber, plastic, etc.) which when compressed offers an increased pressurization of the entrapped fluid within its support membranes 27. The foot pump 26 is characterized by a variety of strategically placed weld lines 80 which serve to create channels through which fluid transfer can take place between the pump 26 and the inflatable bladders 22 and 24. Other welded "darts" 82 may also be used which will aid in reducing the thickness in certain areas of the pump 26 to enhance comfort. The pump 26 may be constructed by welding in a foam of a thickness or space provided by the surrounding semi-enclosed pump material, preferably urethane or some other resilient material, whereby the foam is placed in a compressed state initially and when further compressed by the foot will be more resilient and recover quicker than if not compressed.

The foot pump 26 is approximately three and one-half inches in length and three inches in width.

In the ankle brace the two main inflatable bladders 22 and 24 are interconnected with the foot pump 26. In this case, the two bladders 22 and 24 and the pump 26 are formed with one welding process and may be considered one member but is not so limited, and may include bladders which are connected to the pump by other fluid transfer means such as with tubes or valves.

As shown in FIGS. 1, 2, 3 and 8, the main bladders 22 and 24 each have inlet valves 84 and 86 which could be flap-type valves. In such a valve, air drawn in (entering the bladders 22 and 24) forces the valve's sealing flaps, which are normally biased together, apart which allows the air to flow into the valve. Air forced in a direction opposite to the air drawn in (exiting the bladders 22 and 24) forces the flaps together and they create a substantially airtight seal. Other types of valve arrangements may be used such as an air pressure release and bleed valve or inlet valves.

Figure 4:
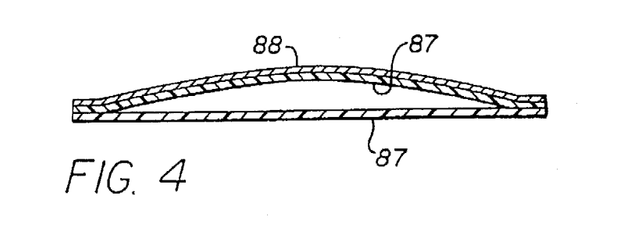
FIG. 4 is a cross-sectional view of one of the main bladders taken along lines 4—4 of FIG. 3.

Thus, as shown in FIG. 4, the main bladders 22 and 24 become inflated when air is directed through their valves 84 and 86. The bladders 22 and 24 expand a maximum width of approximately two an one-half inches. The preferred length of each main bladder 22 and 24 is approximately ten and one-half inches long and is approximately three and three-quarters inches wide. As also shown in FIG. 4, the walls 87 of bladder 22 and 24 are constructed of a non-porous resilient material such as Lycra fabric coated with or bonded to a thin layer of urethane. Each wall 87 is approximately 0.015 inch (15 mills) thick and is capable of stretching under force to allow the bladders a variety of widths to accommodate a wider foot base. Further, a fabric coating 88, for example, Nylon-Lycra, may be laminated to the plastic film that makes up the bladders 22 and 24 to allow the skin to breathe and to increase comfort to the user. This fabric coating 88 may be approximately 0.002 inch (2 mills) thick.

Figure 5:
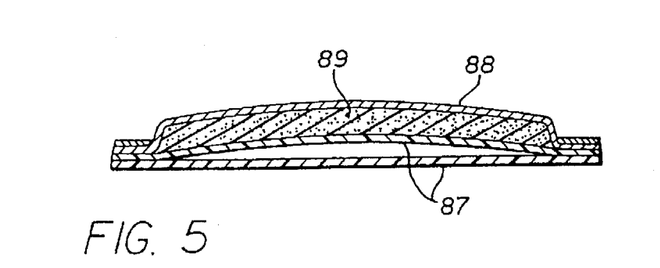
FIG. 5 is a cross-sectional view of one of the additional bladders and a cushioning member of the bladder taken along lines 5—5 of FIG. 3.

FIG. 5 shows a portion of the bladder that includes additional foam padding 89 which is located at the bottom half of each main bladder 22 and 24. This padding 89 is about five inches in length and provides further comfort to the region surrounding the ankle.

Figure 3:
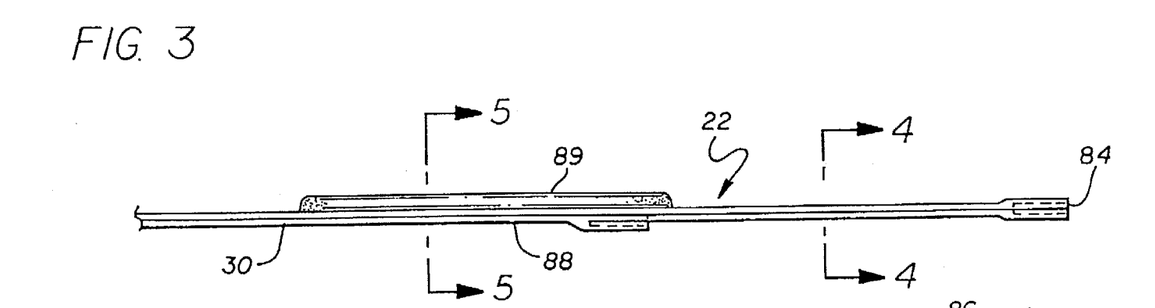
FIG. 3 is a partial side view of the bladder and pump arrangement taken along lines 3—3 of FIG. 2.

As shown in FIGS. 1, 2 and 3 two more smaller inflatable bladders 30 and 32 may be placed distally upon the main inflatable bladders 22 and 24 to provide cushioning and support as well as protect the injured limb from the rigid support shell should either main bladder 22 and 24 puncture. Alteratively, these additional bladders 30 and 32 may also be made to pulsate and the longer main bladders 22 and 24 may serve as non-pulsating protective membranes. The smaller bladders 30 and 32 may be comprised of the same material and consist of the same valve arrangement as the main bladders 22 and 24.

The shorter additional bladders 30 and 32 extend from the bottom of the main bladders 22 and 24 to about halfway up towards the upper most portion of the main bladders 22 and 24. The outside surface of each bladder 22, 30, 24 and 32 has a Velcro portion 90 attached to it in order to affix the support member 18 and 20 to the bladders. It should be further mentioned that all bladder arrangements 22, 30, 24 and 30, preferably, are to be distributed with a certain amount of preinflation.

FIGS. 9 through 18 illustrate the principles of this invention and show alternate side support members 18 and 20, which may be used in the assembly of FIG. 7.

Figure 9:
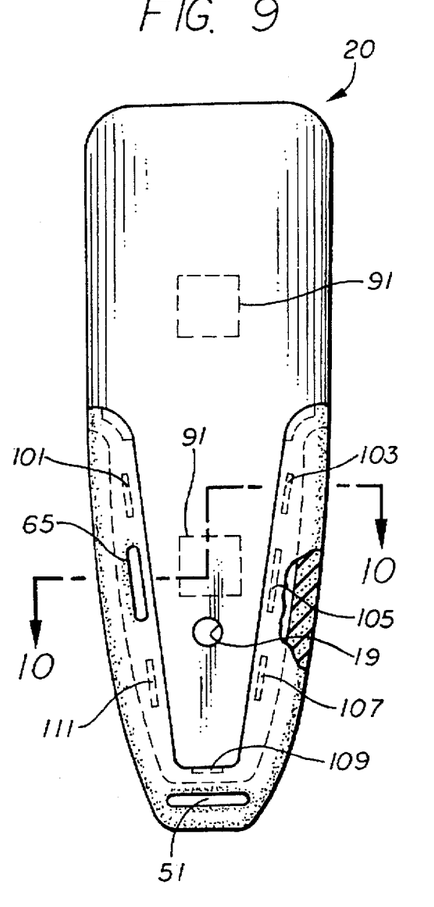
FIG. 9 is a side view of a side support member illustrating the principles of the present invention.
Figure 10:
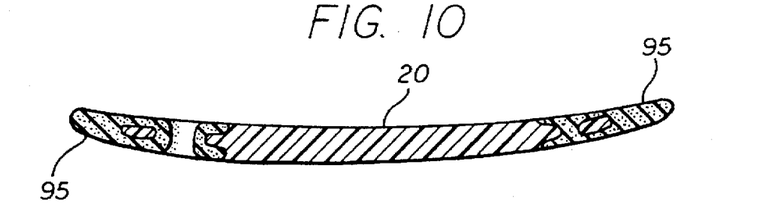
FIG. 10 is a cross-sectional view of the side support taken along lines 10—10 of FIG. 9.

FIGS. 9 and 10 show a support member 20 which is constructed of a rigid polypropylene in one embodiment. Support member 18 may be constructed in an identical manner to support member 20. The support member 20 is slightly curved (see FIG. 10) to better hug and support the ankle. One or more holes 19 for venting any heat that accumulates within the entire ankle brace 16 are also provided. Holes 19 may be used for positioning the part into a mold and also, in some cases, for mechanically securing the resilient material to the support member. The bottom perimeter of each support member 18 and 20 are covered with a flexible padded material 95, preferably vinyl, rubber, or synthetic rubber such as "Santoprene" manufactured by Monsanto, "Kraton" manufactured by Shell, or "Aloryn" manufactured by DuPont, in order to prevent each support 18 and 20 from cutting into the user's lower leg or from puncturing the bladders 22, 23, 24 and 25, and most importantly, to improve the fit of each side support 18 and 20 around the user's lower leg. Support members 18 and 20 may be manufactured of a suitable rigid or semi-rigid material such as Nylon or Glass reinforced nylon by DuPont or High Density Polyethylene (HDPE) made by Dow Chemical Co.

Flexible resilient or padding material 95 may be bonded to support members 18 and 20 by a permanent or semi-permanent adhesive. The flexible padded material 95 may also be formed in place around support members 18 and 20, or may be thermally bonded in place. The material 95 may, for example, be rubber or other similar material.

Openings such as slots 51 and 65 may be included in support member 20 in order to allow straps to be passed through the side support 20. In addition, slots 101, 103, 105, 107, 109, and 111, or others, may be provided to allow mechanical interlocking of the resilient or padding material 95 to secure material 95 to side support 20. Slots 101, 103, 105, 107, 109, and 111 may be replaced by suitable grooves, channels or other suitable interlocking arrangements which can be readily mated with the resilient material 95 which is positioned against side support 20.

In this manner, the resilient material and the side support may be interlocked without requiring the use of additional mechanical fasteners such as straps, tape, cement or the like. However, cement or heat bonding is preferred to supplement the mechanical interlocking.

Additionally, the inner surface of each side support 18 and 20 may include a strip or strips of Velcro material 91 to allow the side supports a means of attaching themselves to the Velcro portions 90 of each bladder or other padding.

Figure 11:
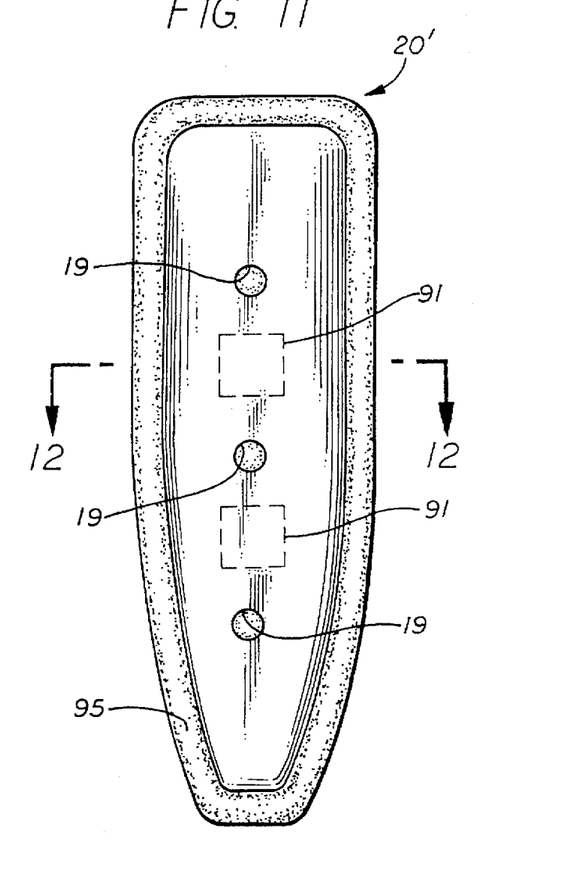
FIG. 11 is a side view of a different embodiment of a side support member illustrating the principles of the present invention.
Figure 12:
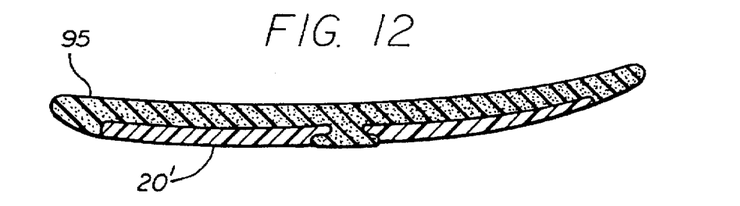
FIG. 12 is a cross-sectional view of the side support of FIG. 11 taken along lines 12—12 of FIG. 11.

FIGS. 11 and 12 show the support member 20' similar to the support member shown in FIGS. 9 and 10 except that the support is secured on top of a flexible cushioning material 95 having a slightly larger area than the side support 20 but is substantially the same shape as the side support, more securing boles 19 are present, and the strap slots 51, 65, 101, 103, 105, 107, 109, and 111 have been removed.

Figures 13, 14, 15:
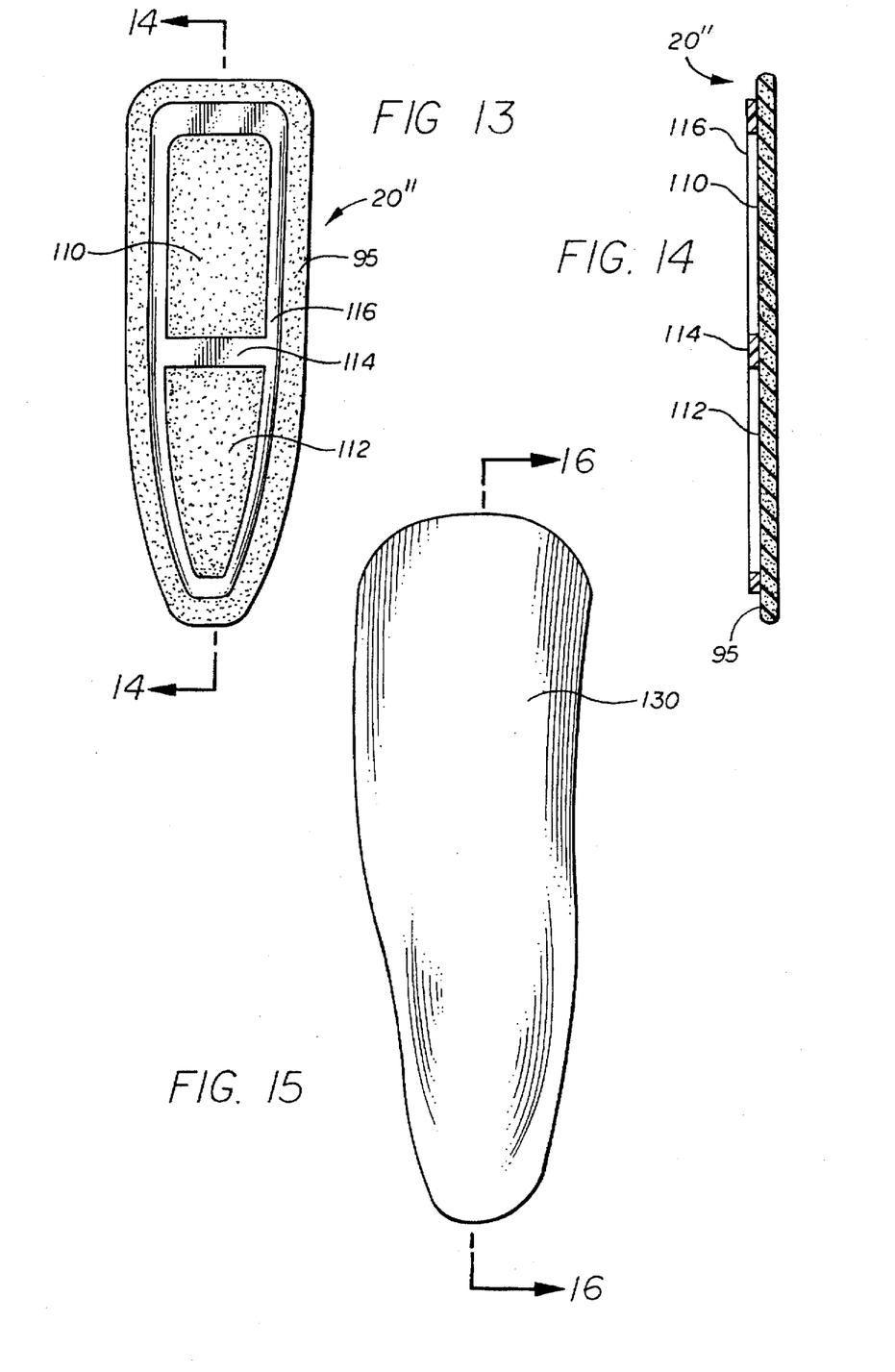
FIG. 13 is a side view of an alternative embodiment of a side support member of the present invention.
FIG. 14 is a cross-sectional view of the embodiment shown in FIG. 13.
FIG. 15 is a side view of an alternative embodiment of a side support member of the present invention.

Alternative embodiments shown in FIGS. 13–14 and 17–18 illustrate side supports 20" and 20"', respectively similar to the side supports shown in FIG. 9–12, except that the side support is reduced in mass by forming a structural frame instead of a solid surface. The structural support consists of peripheral members 116 (FIGS. 13, 14) and 116 (FIGS. 17 and 18) which extend around the perimeter of the side support 20. Single support members 20" and 20"' are illustrated, however, the support members for the opposing side of the ankle are constructed in the same manner. In FIGS. 13 and 14 openings 110 and 112 are present in the upper and lower portions of the support member 20", and a lateral structural member 114 is located between openings 110 and 112 to add strength to the framework 116.

Figure 17:
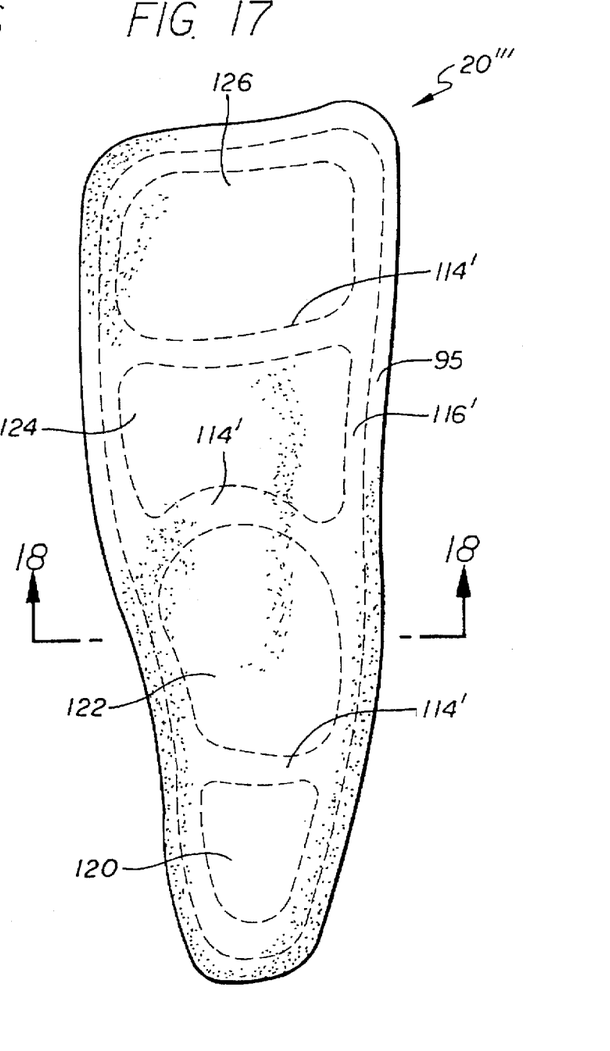
FIG. 17 is a side view of a further alterative embodiment of a side support member of the present invention.
Figure 18:
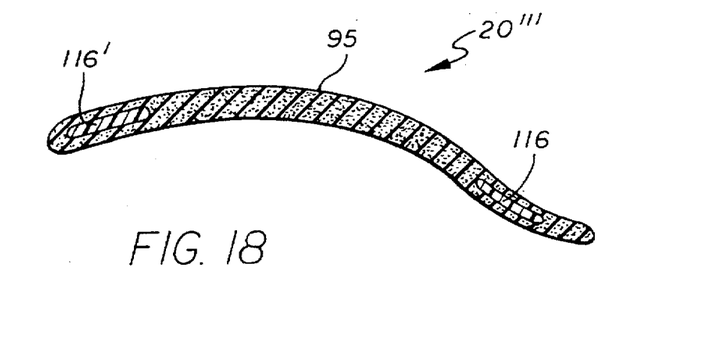
FIG. 18 is a transverse cross sectional view of the embodiment shown in FIG. 17, taken along lines 18—18 of FIG. 17.

In FIGS. 17 and 18, structural members of the three transverse members 114' add strength to the perimeter frame 116 of the side support 20"'. Thus, additional structural members can be employed to increase the structural strength and integrity of the side support 201"' without significantly increasing the weight of this support member. The configurations shown in FIGS. 13 and 17 have a weight which is reduced from the weight of side supports as shown in FIGS. 9–12, because of the material which is removed in forming openings 110, 112, 120, 122, 124, and 126. This configuration also allows the reduction in pressure in specific areas such as the malleoli or ankle bones, see area 112 in FIG. 13, and 122 in FIG. 17.

As shown in FIGS. 13 and 17, the entire perimeter of support member 20 is covered with a flexible resilient or padded material 95 in order to prevent the support members 18 and 20 from cutting into the user's lower leg, or from puncturing the bladders 22, 23, 24, and 25, and to improve the fit of each side support 18 and 20 around the user's lower leg.

It is recognized that the more rigid molded material as shown in FIGS. 9–14 may be constructed using new plastic molding techniques to include a material which is more rigid towards the center, and is extremely flexible or pliable towards the edges. This material may readily replace the use of a two piece assembly shown in FIGS. 9–18. This technique would be especially useful when employed with the configuration shown in FIGS. 9–12, wherein a more flexible, pliable layer of plastic may coat the inside surface of the side support 20 as shown in FIG. 12. This pliable material may replace the flexible material 95 in this configuration, forming a single, integral assembly which includes both a more rigid material such as a high strength reinforced plastic structural strength and a more flexible material for comfort.

Figure 16:
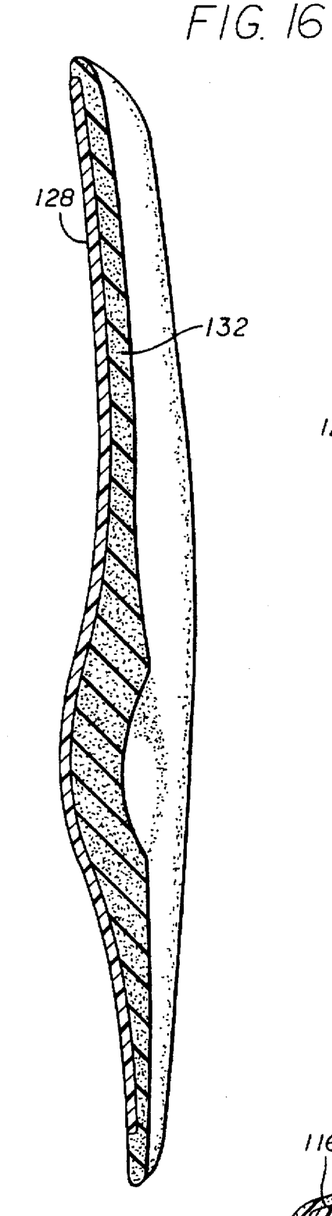
FIG. 16 is a longitudinal cross section view of the embodiment shown in FIG. 15.

In the embodiment shown in FIGS. 15 and 16, side support 128 is formed to accommodate the "bulge" of the ankle of the wearer. Flexible or resilient material 132 is shaped or formed to complement the shape of side support 128 and provide padding between the ankle of a wearer and side support 128. The showing of FIG. 15 is a view of the outside 130 of the ankle brace of FIG. 16. Flexible material 132 may be formed integrally with side support 128, or may be integrally bonded thereto, as shown in FIG. 16. The material 132 may be a soft vinyl foam or a thermoplastic elastomer of the type sold under the trademark "SANTOPRENE."

In the embodiments shown in FIGS. 9 and 10, a single plastic body having a more rigid central portion and grading into a more flexible plastic around the outer edges of side support 20 may be employed. This combination may eliminate-the need for separate padded or resilient material 95, thereby reducing the thickness of the edges of side support 20. This may result in a side support which has a uniform thickness and is more flexible towards the edges of the side support 20 and more rigid towards the center. It is recognized that this technique may be applied to all of the edges of side support 20 in the configurations of FIGS. 9–18.

In another embodiment of the present invention, either side support 18 or 20 may be applied to the ankle of the wearer by the use of one or more straps fastening a single side support to the leg of the user. This configuration can be successfully employed to treat less severe ankle injuries while reducing the weight and bulkiness of the brace which must be worn by the user. Preferably the side support is located on the side of the leg of the wearer to provide the greatest support to the ankle, and immobilize the ankle against particular undesired rotation based on the nature of the ankle injury.

For many users, it is additionally desirable to place a padded material between the ankle and the straps that surround the lower leg, holding the side support 18 or 20 against the lower leg of the wearer.

The operation of the ankle brace 16 in conjunction with air bladders would be as follows: the bladder and pump arrangement is to be attached to the inside of the side supports 18 and 20. If the brace 16 has been previously used, the bottom strap 33 and the counter strap 60 would already have been adjusted. If not, the wearer would position the side supports 18 and 20 to both sides of the ankle, and then after the side supports 18 and 20 are properly positioned, the ankle brace 16 would be held in place using the strap members 34 and 36. The bottom strap 33 would then be adjusted by peeling the Velcro material 35 back from the corresponding Velcro 54 and 56 and pulling up both sides of the strap 33 until the bottom of the side supports are firmly in position. The ends of the strap 35 would then be firmly pressed down on the Velcro 54 and 56 to lock the strap in 33 in position. Similarly the counter strap 60 would be adjusted to pull the back lower end of the side supports 18 and 20 together above the heel.

The shoe would now be fitted over the entire ankle brace 16, as shown in FIG. 7, and the laces laced through the holes 70 or in other fastening means located at the lower end of the side supports 18 and 20. The laces would then be pulled tightly and tied, again as shown in FIG. 7, so that the ankle brace 16 is firmly in position.

Subsequently the bladders 22, 30, 24 and 32 are inflated to their therapeutically desired pressure by using, for example, an attachable hand-held pump.

Therefore, while in use, the fluid within the pressurized ankle support bladders 22, 30, 24 and 32 and the interconnected preinflated foot pump is displaced back and forth between either the main bladders 22 and 24 and/or the shorter bladders 30 and 32 thereby creating a pulsing action which lends to a massaging compression effect that helps reduce swelling and atrophying and increases venous and lymphatic return throughout the lower leg while effectively preventing inversion, eversion and anterior subluxation of the ankle.

Figure 19:
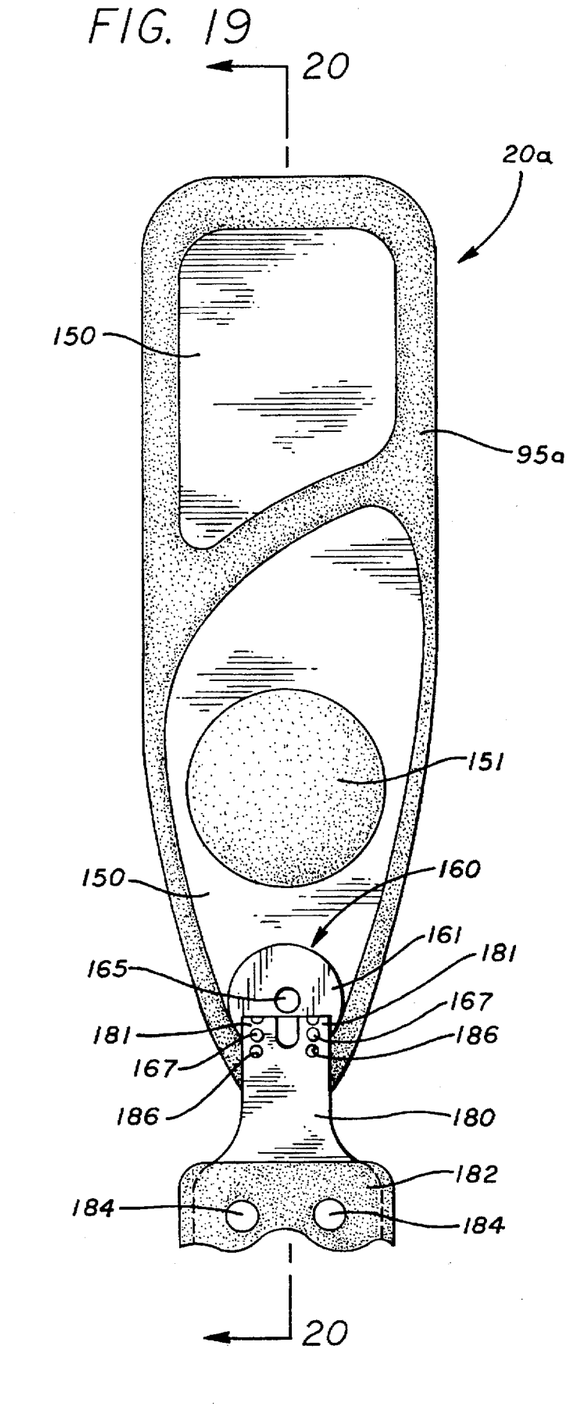
FIG. 19 is a side view of another alternative embodiment of a side support member.
Figure 20:
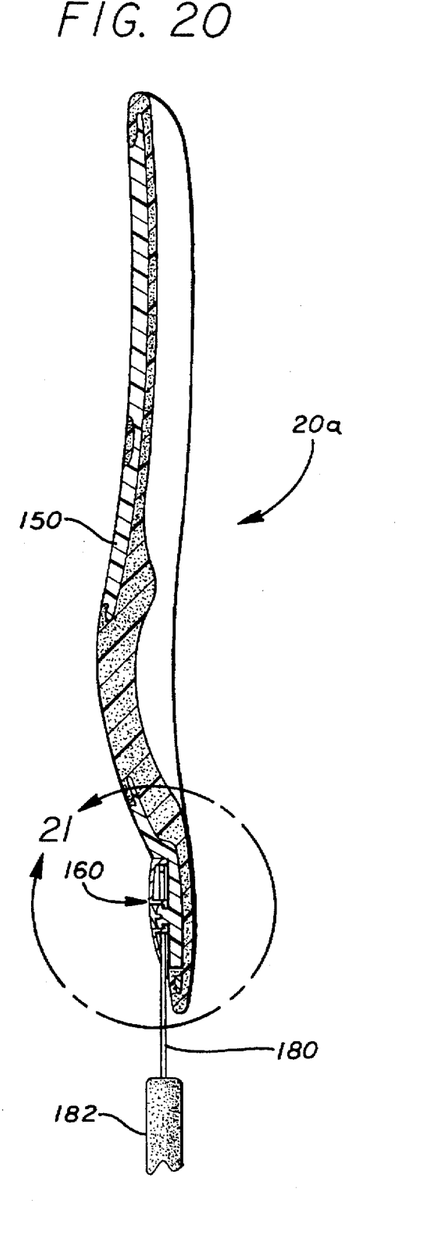
FIG. 20 is a longitudinal cross sectional view of the side support taken along line 20—20 of FIG. 19.
Figure 21:
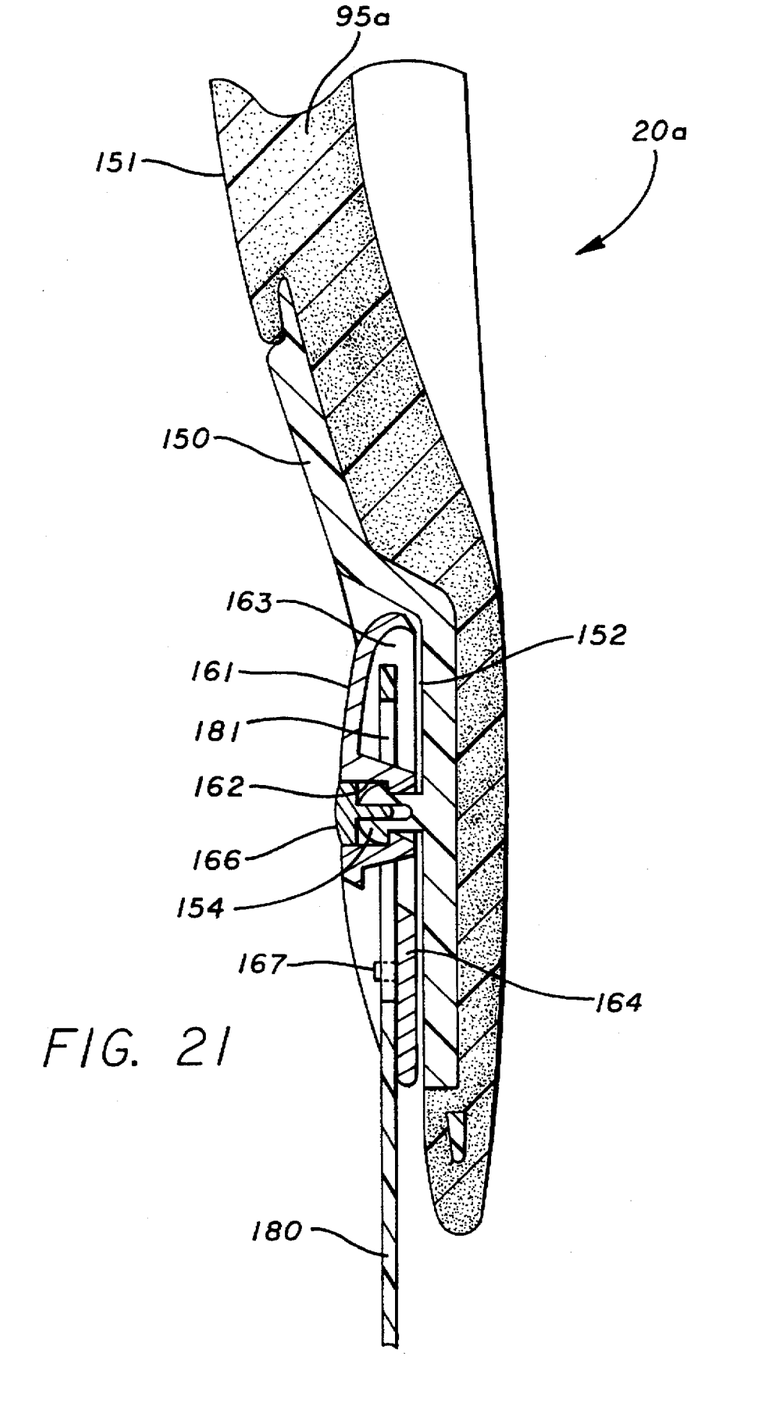
FIG. 21 is a an enlarged detail view of the section defined by circular line 21 of FIG. 20.

Another alternative embodiment shown in FIGS. 19–21 illustrates side supports 20a, similar to the side supports shown in FIGS. 9–15, that includes, at the lower end of the side support frame 150, a pivot disc 160 with attachment pins 167 to allow heel strap 180 to be adjustably attached to the side supports 20a.

FIGS. 19–20 show that in this implementation, the side support 20a is formed with a structural frame 150 which surrounds but does not cover the ankle or malleolus area 151. The ankle area 151 is only covered by the resilient flexible material 95a.

FIGS. 19 and 21 show a pivot disc 160 mounted to the lower end of a side support frame 150 at the pivot point 165. The lower end of a side support frame 150 comprises a circular recess 152 to receive the circular pivot disc 160. The pivot disc 160 may be coupled to the frame 150 using a mechanical interlock or a cap 166. For a mechanical interlock coupling, the recessed area 152 of the frame 150 has a protruding pin 154 at the center of the recessed area with which an opening 162 in the center of pivot disc 160 is interlocked by mating shoulders on the pin 154 and the opening 152. A cap 166 may serve as a supplemental coupling to secure the pivot disc 160 to the side support frame 150.

As shown more clearly in FIG. 21, the pivot disc 160 may have an upper portion 161 which may be formed to create a cavity 163 between it and the recessed area formed by the portion of the side support frame 152, and a lower portion 164 to which pins 167 are affixed. In this implementation, the cavity may function as clearance to receive the ends of the heel strap 180 which have been divided into two strips 181 with holes 186 to be selectively coupled to the pins 167.

The heel strap 180 is made of flexible resilient material such that the effective length of the heel strap can be adjusted to fit the width of the heel being protected. FIGS. 19 and 21 show the heel strap 180 and the heel pad 182 that may be attached to the strap to increase the cushioning of the heel. Holes 184 may be used to mechanically interlock the strap 180 and the pad 182 by molding the pad through the holes. Each end of the heel strap 180 may be slotted to form two strips 181 which straddle the pivot point 165. Each strip 181 contains several holes, aligned with corresponding holes of the other strip at the same end, which are used to adjustably attach the heel strap 180 to pivot disc 160.

Instead of the pins 167 and the holes 186, Velcro type hook and loop pads may be employed to adjustably attach the heel strap 180 to the pivot disc 160.

While FIGS. 1-8 relate to the combination using bladders, it is to be understood that the arrangements of FIGS. 9-18 may be employed using gel or foam rubber pads, for example, between the side members and the ankle, or in some cases with no additional padding.

Although the invention has been described with reference to particular embodiments, it is to be appreciated that other adaptations and modifications may be used without departing from the spirit and scope of the present invention. For example, in FIG. 8 a heel cup 100 which may or may not be inflatable may be included to provide further support to the ankle region. Also, a possible extra bladder surrounding the ankle may be incorporated into the brace 16 to contain gel or water, with or without foam, for hot or cold therapy. In addition, the heel strap may have a series of central holes which may encompass the pivot point with the length of the strap being adjustable by selecting different holes through which the pivot structure extends.

Accordingly, the present invention is not limited to the constructions precisely as shown in the drawings or described in the detailed description.

What is claimed is:

1. An improved ankle brace for restraining the ankle against inversion and eversion while allowing plantarflexion and dorsiflexion, comprising:
   a pair of substantially rigid side supports having upper and lower ends, preformed of a relatively rigid material to conform to the shape of the lower leg, for fitting about the lower leg, said side supports having a configuration to encase both sides of the ankle;
   said side supports having a flexible resilient material integrally secured to said side supports to improve the fit of said side supports around the user's lower leg;
   a flexible heel strap extending between the lower ends of said side supports;
   said heel strap being adjustably and pivotally attachable to the lower ends of each of said side supports; and
   wherein said lower end of said side supports comprise a pivoting structure which comprises: a) a pivot disc; and b) a coupling for rotatably mounting said pivot disc to said side supports.

2. An ankle brace as defined in claim 1 wherein the pivot point is adapted to be below the malleolus of the user.

3. An ankle brace as defined in claim 1 wherein said side supports include a structural frame having a malleolar opening adapted to be positioned surrounding the user's malleolus when the brace is worn by the user and flexible resilient material extending over the malleolar opening.

4. An ankle brace as defined in claim 1 wherein the loser ends of said side supports can be inserted into the sides of a shoe.

5. An ankle brace as defined in claim 1 wherein two pins or hook/loop fasteners are affixed to said pivot disc to removably secure said heel strap thereto.

6. An ankle brace as defined in claim 1 wherein said heel strap comprises:
   a heel pad of a resilient material removably attached to the center portion of said heel strap;
   a relatively wide center portion to be positioned under the heel to which said heel pad is attached; and
   a relatively narrow and thin portions at each end of said heel strap used to attach said heel strap to said side supports.

7. An improved ankle brace for restraining the ankle against inversion and eversion while allowing plantarflexion and dorsiflexion, comprising:
   a pair of substantially rigid side supports having upper and lower ends, preformed of a rigid or a semi-rigid material to conform to the shape of the lower leg, for fitting about the user's lower leg, said side supports having a configuration to encase both sides of the ankle;
   said side supports having a flexible, resilient cushioning material integrally secured to said side supports to improve the fit of said side supports around the user's lower leg;
   said side supports comprising structural frame having a malleolar opening adapted to be positioned surrounding the user's malleolus when the brace is worn by the user; and
   a flexible pivoting heel strap, attachable to said side supports, extending between the lower ends of said side supports.

8. An ankle brace as defined in claim 7 wherein only said cushioning material of the brace covers the malleolus of the user when the brace is worn by the user.

9. An ankle brace as defined in claim 7 wherein the lower ends of said side supports are adapted to be inserted into the sides of a shoe of the user.

10. An ankle brace as defined in claim 7 wherein the lower ends of said side supports include a pivot disc pivotally mounted and adjustably receiving said flexible pivoting heel strap.

11. An improved ankle brace for restraining the ankle against inversion and eversion while allowing plantarflexion and dorsiflexion, comprising:
   a pair of substantially rigid side supports having upper and lower ends, formed of a rigid or semi-rigid material to conform to the shape of the lower leg, for fitting about the lower leg, said side supports having a configuration to encase both sides of the ankle;
   straps for securing said side supports to the ankle and the lower leg;
   a flexible heel strap, attachable to and extending between the lower ends of said side supports; and
   a pivot disc pivotally mounted on the lower end of said side support and adjustably receiving said flexible heel strap.

12. An ankle brace as defined in claim 11 wherein the lower end of said side support includes a circular depression within which said pivot disc rotates; and a coupling in the center of said depression for mechanically securing said pivot disc and forming the pivot point.

13. An ankle brace as defined in claim 11 wherein said pivot disc further comprises:

a hole in the center for interlocking with the lower end of said side supports; and means affixed to said pivot disc for removably attaching said heel strap.

14. An ankle brace as defined in claim 11 wherein said pivot disc is coupled to the pivot frame using mechanically interlocking parts.

15. An ankle brace as defined in claim 11 wherein the center of said pivot disc, the pivot point, is adapted to be below the malleolus of the user.

16. An ankle brace as defined in claim 11 wherein said heel strap further comprises:

a heel pad of a resilient material attached to the center portion of said heel strap;

a relatively wide center portion to be positioned under the heel to which a pad is attached;

a relatively narrow end portions at each end of said strap forking into two strips to form a divided end, straddling the pivot point; and each of said strips having several holes, aligned with corresponding holes of the other strip of the same end, adjustably attachable to said pivot disc.

17. An improved ankle brace for restraining the ankle against inversion and eversion while allowing plantarflexion and dorsiflexion, comprising:

a pair of side supports having upper and lower ends, preformed of a relatively rigid material to conform to the shape of the lower leg, for fitting about the lower leg, said side supports having a configuration to encase both sides of the ankle;

a flexible heel strap extending between the lower ends of said side supports;

said heel strap being adjustably and pivotally attachable to the lower ends of each of said side supports; and a pivot disc mounted on the lower end of each of said side supports, each said pivot disc being pivotally mounted and adjustably receiving said flexible heel strap.

18. An ankle brace as defined in claim 17 wherein said side supports have flexible material integrally secured to said side supports to improve the fit and comfort of said side supports around the lower leg.

19. An ankle brace for restraining an ankle of a patient against inversion and eversion while allowing plantarflexion and dorsiflexion, comprising:

a pair of side supports, said side supports being configured to fit about a lower leg of a patient, to conform to the shape of the lower leg, and to encase both sides of an ankle of the patient; and a flexible heel strap pivotally attached to pivot points at lower ends of said side supports, said flexible heel strap extending between said lower ends, said flexible heel strap having its effective length being adjustable to accommodate for different heel widths of different patients.

20. An ankle brace as defined in claim 19 wherein said side supports include a flexible resilient material to improve the fit of said side supports around the lower leg.

21. An ankle brace as defined in claim 19 wherein said flexible heel strap includes a cushioning heel pad.

22. An ankle brace as defined in claim 19 further comprising a pivot disc pivotally attaching an end of said flexible heel strap to one of said side supports.

23. An ankle brace as defined in claim 22 wherein the end of said flexible heel strap is adjustably attachable to said pivot disc to thereby adjust the effective length of said flexible heel strap.

24. An ankle brace as defined in claim 19 wherein the pivot points are fixed relative to the lower ends.

25. An ankle brace as defined in claim 19 wherein at least one end of said flexible heel strap is adjustably positionable relative to the respective pivot point to thereby adjust the effective length of said flexible heel strap.

26. An ankle brace as defined in claim 19 wherein the length of said flexible heel strap from one end thereof to another is constant and the effective length is varied by adjusting the attachment location of said flexible heel strap relative to at least one of the pivot points.

* * * * *